United States Patent
Patangay et al.

(10) Patent No.: US 8,187,199 B2
(45) Date of Patent: May 29, 2012

(54) MYOCARDIAL CONTRACTILE RESERVE MEASURED DURING ACTIVITIES OF DAILY LIVING

(75) Inventors: Abhilash Patangay, Inver Grove Heights, MN (US); Kenneth C. Beck, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 51 days.

(21) Appl. No.: 12/903,724

(22) Filed: Oct. 13, 2010

(65) Prior Publication Data

US 2011/0105922 A1    May 5, 2011

Related U.S. Application Data

(60) Provisional application No. 61/258,480, filed on Nov. 5, 2009.

(51) Int. Cl.
*A61B 5/02* (2006.01)
(52) U.S. Cl. ........ 600/508; 600/483; 600/526; 600/587; 607/9; 607/19; 128/898
(58) Field of Classification Search .......... 600/483, 600/508, 526, 587; 607/9, 19; 128/898
See application file for complete search history.

(56) References Cited

U.S. PATENT DOCUMENTS

| 5,991,661 | A  | 11/1999 | Park et al. |
| 7,509,166 | B2 | 3/2009 | Libbus |
| 7,664,547 | B2 | 2/2010 | Plicchi et al. |
| 2007/0021678 | A1 | 1/2007 | Beck et al. |
| 2008/0114256 | A1 | 5/2008 | Zhang et al. |
| 2008/0119750 | A1 | 5/2008 | Patangay et al. |
| 2008/0154144 | A1 | 6/2008 | Unver et al. |
| 2008/0177156 | A1 | 7/2008 | Zhang et al. |
| 2010/0049063 | A1 | 2/2010 | Dobak, III et al. |
| 2010/0057155 | A1 | 3/2010 | Farazi et al. |
| 2010/0094370 | A1 | 4/2010 | Levin et al. |

OTHER PUBLICATIONS

Ciampi, Quirino, et al., "Identification of responders to cardiac resynchronization therapy by contractile reserve during stress echocardiography", Eur J Heart Fail., 11(5), (May 2009), 489-96.
Lancellotti, Patrizio, et al., "Myocardial contractile reserve during exercise predicts left ventricular reverse remodelling after cardiac resynchronization therapy.", Eur J Echocardiogr., 10(5), (Jul. 2009), 663-8.
Lim, Pascal, et al., "Importance of contractile reserve for CRT", Europace, 9(9), (Sep. 2007), 739-43.
Naqvi, Tasneem Z., et al., "Myocardial contractile reserve on dobutamine echocardiography predicts late spontaneous improvement in cardiac function in patients with recent onset idiopathic dilated cardiomyopathy", J Am Coll Cardiol., 34(5), (Nov. 1, 1999), 1537-44.
Otasevic, Petar, et al., "Right vs. left ventricular contractile reserve in one-year prognosis of patients with idiopathic dilated cardiomyopathy: assessment by dobutamine stress echocardiography.", Eur J Echocardiogr., 6(6), (Dec. 2005), 429-34.
Scrutinio, D., et al., "Low-dose dobutamine responsiveness in idiopathic dilated cardiomyopathy: relation to exercise capacity and clinical outcome", Eur Heart J., 21(11), (Jun. 2000), 927-34.

*Primary Examiner* — Carl H Layno
*Assistant Examiner* — Yun Haeng H Lee
(74) *Attorney, Agent, or Firm* — Schwegman, Lundberg & Woessner, P.A.

(57) ABSTRACT

A contractile reserve indicator, corresponding to a predicted value of a maximum change in myocardial contractility that can be achieved by a subject, can be determined using a detected indication of cardiac contractility across various different physical activity levels.

20 Claims, 5 Drawing Sheets

| ACTIVITY | HR | S1 | PP | dP/dT |
|---|---|---|---|---|
| 120 | 109 | 37 | 16 | 3000 |
| 110 | 102 | 34 | 15 | 2600 |
| 100 | 97 | 31 | 14 | 2200 |
| 90 | 94 | 29 | 14 | 2000 |
| 80 | 92 | 27 | 13 | 1800 |
| 70 | 88 | 25 | 14 | 1500 |
| 60 | 84 | 23 | 13 | 1600 |
| 50 | 80 | 20 | 12 | 1400 |
| 40 | 76 | 18 | 12 | 1500 |
| 30 | 73 | 16 | 11 | 1300 |
| 20 | 68 | 15 | 12 | 1400 |
| 10 | 63 | 12 | 10 | 1300 |
| 0 | 60 | 10 | 10 | 1300 |

MYOCARDIAL CONTRACTILE RESERVE MEASURED DURING ACTIVITIES OF DAILY LIVING

CROSS-REFERENCE TO RELATED APPLICATION

This application claims the benefit of U.S. Provisional Application No. 61/258,480, filed on Nov. 5, 2009, under 35 U.S.C. §119(e), which is incorporated herein by reference in its entirety.

BACKGROUND

Myocardial contractility, or cardiac contractility, is a term that can be used to describe the performance of cardiac muscle. In other words, cardiac contractility can refer to the intrinsic ability of cardiac muscle fiber to contract at a given fiber length. Changes in the ability of cardiac muscle to produce force during contraction can result from different degrees of binding between myosin and actin filaments, the core components of muscle fiber. The degree of binding that occurs between these filaments can depend on the concentration of calcium ions in cardiac muscle cells, which, in turn, can be controlled by the sympathetic nervous system. Furthermore, cardiac muscle sensitivity to calcium ions (e.g. calcium ion receptor binding affinity) can also affect cardiac contractility.

Contractile reserve (CR), as defined in this document, is the predicted maximum change in cardiac contractility that can be achieved by a patient. In general, patients with a higher CR may achieve greater improvement in cardiac function after cardiac resynchronization therapy (CRT) than patients with a lower CR. Determining an indication of a patient's CR may therefore be used to assess patient status, assess patient response to therapy, and adjust therapy selection.

CR can be measured using a dobutamine stress test. Dobutamine is an inotropic agent, which causes an increase in heart rate and blood pressure similar to the effects of exercise. The dobutamine stress test includes an echocardiogram done at rest and again at peak heart rate after dobutamine has been administered intravenously. A measured change in contractility between rest and peak heart rate can be used as an indication of CR. Other ways of measuring CR include performing an exercise stress test, using various pacing modalities, and using neural therapies.

OVERVIEW

Myocardial contractile reserve can be used to predict the ability of the myocardium to improve performance. This document describes, among other things, a system and method of determining a contractile reserve indicator, corresponding to a predicted value of a maximum change in myocardial contractility that can be achieved by a subject, by using a detected indication of cardiac contractility across various different physical activity levels.

Example 1 describes a system. In this example, the system comprises a physical activity sensor, configured to detect a physical activity signal from a subject; a cardiac contractility sensor, configured to detect an indication of cardiac contractility from the subject; a processor, coupled to the cardiac contractility sensor and the physical activity sensor, the processor configured to determine a contractile reserve indicator using a characteristic of a function of the indication of cardiac contractility across various different activity levels, wherein the contractile reserve indicator corresponds to a predicted value of a maximum change in contractility that can be achieved by the subject; and a memory, coupled to the processor and configured to receive and store the contractile reserve indicator to be provided to a process or a user.

In Example 2, the system of Example 1 optionally comprises the processor configured to use the physical activity signal to define time periods corresponding to different steady-state activity levels, wherein the processor is configured to determine the contractile reserve indicator using a characteristic of a function of the indication of cardiac contractility across the different steady-state activity levels.

In Example 3, the system of one or more Examples 1-2 optionally comprises the physical activity sensor configured to include at least one of an accelerometer or a heart rate sensor.

In Example 4, the system of one or more of Examples 1-3 optionally comprises the cardiac contractility sensor configured to detect the indication of cardiac contractility using at least one of: a pulse pressure, a rate of change of blood pressure during a cardiac ejection period, a rate of change of intraventricular blood pressure during a cardiac ejection period, a S1 heart sound magnitude, a pre-ejection period, or a change in cardiac stroke.

In Example 5, the system of one or more of Examples 1-4 optionally comprises the cardiac contractility sensor configured to detect the indication of cardiac contractility using a pulse pressure.

In Example 6, the system of one or more of Examples 1-5 optionally comprises the cardiac contractility sensor configured to detect the indication of cardiac contractility using a rate of change of blood pressure during a cardiac ejection period.

In Example 7, the system of one or more of Examples 1-6 optionally comprises the cardiac contractility sensor configured to detect the indication of cardiac contractility using a rate of change of intraventricular blood pressure during a cardiac ejection period.

In Example 8, the system of one or more of Examples 1-7 optionally comprises the cardiac contractility sensor configured to detect the indication of cardiac contractility using a S1 magnitude.

In Example 9, the system of one or more of Examples 1-8 optionally comprises the cardiac contractility sensor configured to detect the indication of cardiac contractility using a pre-ejection period.

In Example 10, the system of one or more of Examples 1-9 optionally comprises the cardiac contractility sensor configured to detect the indication of cardiac contractility using a change in cardiac stroke.

In Example 11, the system of one or more of Examples 1-10 optionally comprises at least a portion of the system being implantable.

In Example 12, the system of one or more of Examples 1-11 optionally comprises at least a portion of the system being included in an external carrier capable of being affixed to skin of the subject.

In Example 13, the system of one or more of Examples 1-12 optionally comprises the processor configured to classify the subject as one of (1) a therapy responder or (2) a therapy non-responder using the contractile reserve indicator.

In Example 14, the system of one or more of Examples 1-13 optionally comprises a dyssynchrony sensor configured to detect an indication of cardiac dyssynchrony from the subject, the dyssynchrony sensor coupled to the processor; wherein the processor is configured to: determine a dyssynchrony indicator using the indication of cardiac dyssynchrony; and determine a diagnostic indicator using both the dyssynchrony indicator and the contractile reserve indicator; and wherein the memory is coupled to receive and store the diagnostic indicator to be provided to a user or process.

In Example 15, the system of Example 14 optionally comprises the dyssynchrony sensor configured to detect an indication of cardiac dyssynchrony using at least one of an electrocardiogram, an intracardiac impedance, an indication of heart wall motion, or a magnitude of a heart sound.

In Example 16, the system of one or more of Examples 14-15 optionally comprises the processor configured to classify the subject as one of (1) a therapy responder or (2) a therapy non-responder using the dyssynchrony indicator and the contractile reserve indicator.

In Example 17, the system of one or more of Examples 1-16 optionally comprises a therapy circuit, coupled to the processor, the therapy circuit configured to provide a therapy to the subject; and wherein the processor is configured to control the therapy provided by the therapy circuit using information about the contractile reserve indicator.

In Example 18, the system of Examples 17 optionally comprises the therapy circuit configured to include at least one of a cardiac resynchronization therapy circuit, a neuromodulation therapy circuit, or a drug therapy control circuit.

In Example 19, the system of one or more of Examples 17-18 optionally comprises the therapy circuit configured to include a cardiac resynchronization therapy circuit.

In Example 20, the system of one or more or Examples 17-19 optionally comprises the processor configured to trigger the therapy circuit to provide therapy when the contractile reserve indicator indicates that the subject exhibits a contractile reserve that is above a specified threshold.

In Example 21, the system of one or more of Examples 17-20 optionally comprises the processor configured to trigger the therapy circuit to withhold therapy when the contractile reserve indicator indicates that the subject exhibits a contractile reserve that is below a specified threshold.

Example 22 describes a method. In this example, the method comprises detecting a physical activity signal from a subject; and detecting an indication of cardiac contractility from the subject; determining a contractile reserve indicator using a characteristic of a function of the indication of cardiac contractility across various different activity levels, wherein the contractile reserve indicator corresponds to a predicted value of a maximum change in contractility that can be achieved by the subject; and providing the contractile reserve indicator to a user or process.

In Example 23, the method of Example 22 optionally comprises using the physical activity signal to define time periods corresponding to different steady-state activity levels; wherein determining a contractile reserve indicator includes using a characteristic of a function of the indication of cardiac contractility across the different steady-state activity levels.

In Example 24, the method of one or more of Examples 22-23 optionally comprises detecting a physical activity signal, including detecting at least one of an acceleration or a heart rate.

In Example 25, the method of one or more of Examples 22-24 optionally comprises detecting an indication of cardiac contractility using at least one of: a pulse pressure, a rate of change of blood pressure during a cardiac ejection period, a rate of change of intraventricular blood pressure during a cardiac ejection period, a S1 heart sound magnitude, a pre-ejection period, or a change in cardiac stroke.

In Example 26, the method of one or more of Examples 22-25 optionally comprises detecting an indication of cardiac contractility using a pulse pressure.

In Example 27, the method of one or more of Examples 22-26 optionally comprises detecting an indication of cardiac contractility using a rate of change of blood pressure during a cardiac ejection period.

In Example 28, the method of one or more of Examples 22-27 optionally comprises detecting an indication of cardiac contractility using a rate of change of intraventricular blood pressure during a cardiac ejection period.

In Example 29, the method of one or more of Examples 22-28 optionally comprises detecting an indication of cardiac contractility using a S1 heart sound magnitude.

In Example 30, the method of one or more of Examples 22-29 optionally comprises detecting an indication of cardiac contractility using a pre-ejection period.

In Example 31, the method of one or more of Examples 22-30 optionally comprises detecting an indication of cardiac contractility using a change in cardiac stroke.

In Example 32, the method of one or more of Examples 22-31 optionally comprises classifying the subject as one of (1) a therapy responder or (2) a therapy non-responder using the contractile reserve indicator.

In Example 33, the method of one or more of Examples 22-32 optionally comprises detecting an indication of cardiac dyssynchrony from the subject; determining a dyssynchrony indicator using the indication of cardiac dyssynchrony; determining a diagnostic indicator using both the dyssynchrony indicator and the contractile reserve indicator; and providing the diagnostic indicator to a user or process.

In Example 34, the method of Example 33 optionally comprises detecting an indication of dyssynchrony using at least one of an electrocardiogram, an intracardiac impedance, an indication of heart wall motion, or a magnitude of a heart sound.

In Example 35, the method of one or more of Examples 33-34 optionally comprises classifying the subject as one of (1) a therapy responder or (2) a therapy non-responder using the dyssynchrony indicator and the contractile reserve indicator.

In Example 36, the method of one or more of Examples 22-35 optionally comprises providing a therapy to the subject; and controlling the therapy using information about the contractile reserve indicator.

In Example 37, the method of Examples 36 optionally comprises providing at least one of cardiac resynchronization therapy, neuromodulation therapy, or drug therapy In Example 38, the method of one or more of Examples 36-37 optionally comprises providing cardiac resynchronization therapy.

In Example 39, the method of one or more of Examples 36-38 optionally comprises providing the therapy to the subject when the contractile reserve indicator indicates that the subject exhibits a contractile reserve that is above a specified threshold.

In Example 40, the method of one or more of Examples 36-39 optionally comprises withholding the therapy from the subject when the contractile reserve indicator indicates that the subject exhibits a contractile reserve that is below a specified threshold.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, a system and method of determining a myocardial contractile reserve indicator, which can be used to predict improvement in patients with cardiac disease.

The present inventors have recognized, among other things, that CR can be measured without the need for intravenous drugs, stress testing, or other complicated testing procedures. Instead, CR can more easily be measured during activities of daily living, such as using one or more sensors of contractility, such as a pulse pressure sensor, a heart sound sensor, or an impedance sensor, for example. It is believed that measuring CR in response to activities of daily living, as opposed to conducting a stress test, can be beneficial because it can be easier for the patient, it can be less time consuming and less expensive, it can be performed in a variety of settings and even at home, and it can be done more frequently, such as on a weekly basis.

Figure 1:
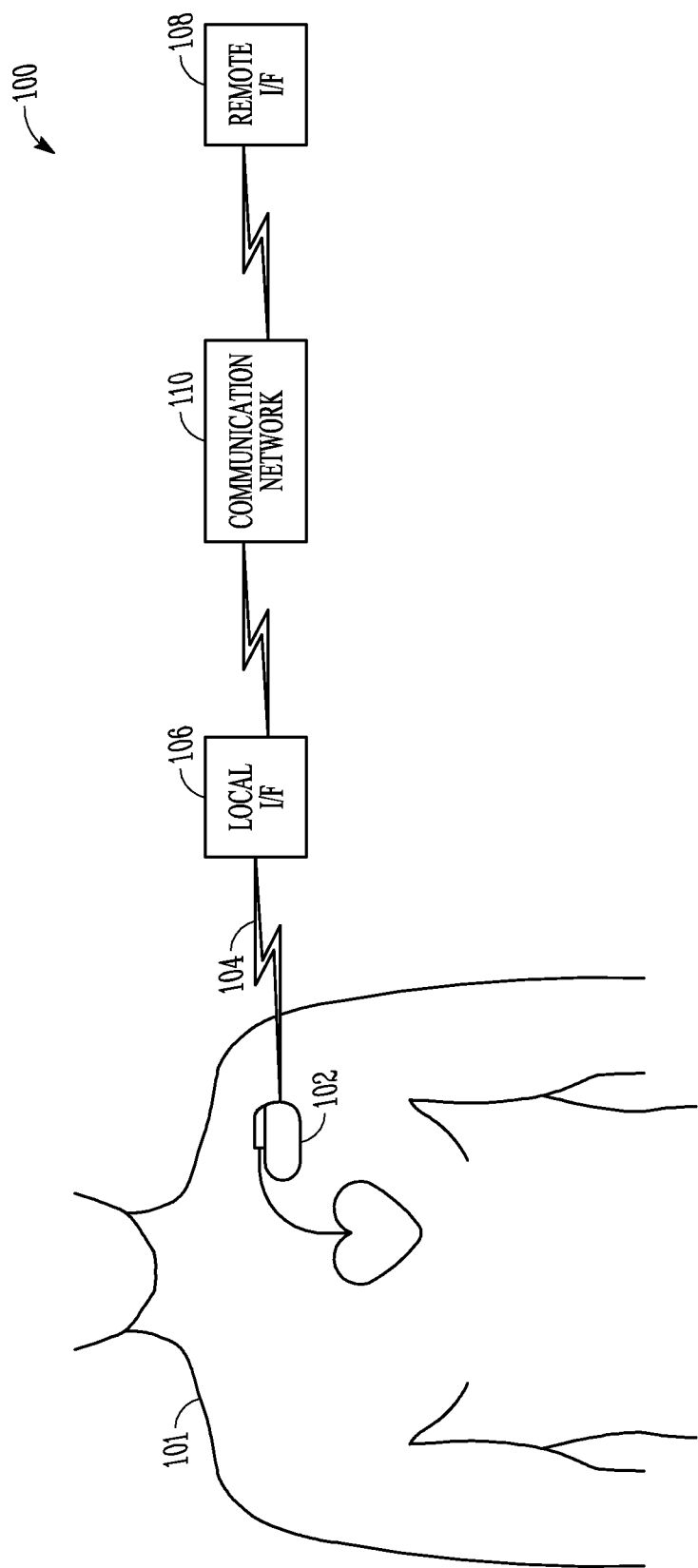
FIG. 1 is schematic diagram illustrating generally an example of a cardiac function management system, such as for use with a human or animal subject.

FIG. 1 is schematic diagram illustrating generally an example of portions of a cardiac function management system 100, such as for use with a human or other living subject 101. In this example, the system 100 can include an implantable or external ambulatory or other cardiac function management (CFM) device 102. Examples of CFM device 102 can include, without limitation, a pacemaker, a cardioverter, a defibrillator, a CRT device, or other cardiac monitoring or therapy delivery device, for example, including a cardiac device that includes or works in coordination with one or more neuro-stimulating devices, or other devices, drugs, drug delivery systems, or other therapies. The CFM device 102 can include a communication circuit, such as for establishing a unidirectional or bidirectional wireless communication link 104 with an external local interface 106, with an implantable or external therapy circuit, or with another device with communication capability. In an example, the external local interface 106 can further unidirectionally or bidirectionally communicate with an external remote interface 108, such as wirelessly or otherwise, such as via a shared communication or computer network 110.

Figure 2:
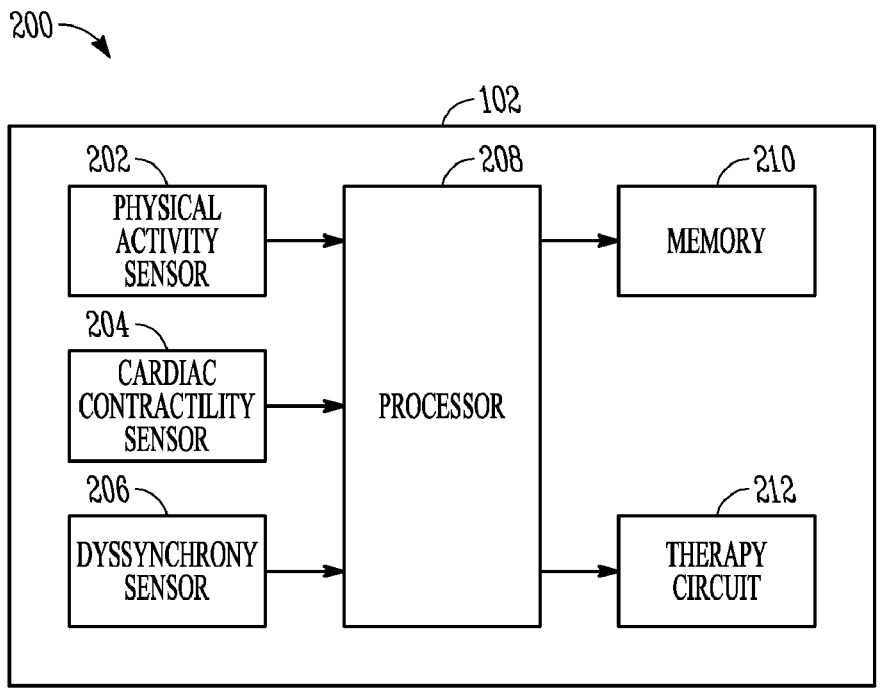
FIG. 2 is a block diagram illustrating generally an example of a system for determining a contractile reserve indicator corresponding to a predicted value of a maximum change in myocardial contractility that can be achieved by a subject.

FIG. 2 is a block diagram illustrating generally an example of portions of a system 200 that can determining a CR indicator corresponding to a predicted value of a maximum change in myocardial contractility that can be achieved by a subject. In this example, the system 200 for determining a CR indicator can be included within the CFM device 102. In certain examples, the system 200 can be included within a monitoring device or other device. In an example, at least a portion of the system 200 can be implantable. In an example, at least a portion of the system 200 can be included in an external ambulatory carrier such as, for example, capable of being worn by a subject or affixed to the skin of a subject, such as a skin patch.

The system 200 can include a physical activity sensor 202, which can be configured to detect a physical activity signal from a subject. The physical activity sensor 202 can include an accelerometer or a heart rate sensor, for example. The system 200 can further include a cardiac contractility sensor 204, which can be configured to detect an indication of cardiac contractility from the subject. The cardiac contractility sensor 204 can be configured to detect a pulse pressure, a rate of change of blood pressure such as during a cardiac ejection period, a S1 heart sound, a pre-ejection period (PEP), a change in cardiac stroke (e.g., a change in the volume of blood in the heart during a cardiac cycle), or a force of a cardiac contraction, for example, or another contractility indicator.

In an example, the cardiac contractility sensor 204 can include a pulmonary artery pressure (PAP) sensor. Pulse pressure can be detected using information about PAP, such as described or incorporated in Zhang et al., U.S. patent application Ser. No. 11/624,974 entitled "ISCHEMIA DETECTION USING PRESSURE SENSOR," now published as U.S. Patent Application Publication No. 2008/0177156, assigned to the assignee of the present patent application, the disclosure of which is incorporated herein by reference in its entirety. In an example, the cardiac contractility sensor 204 can include a pressure sensor such as in a coronary vein. A rate of change of blood pressure, such as during a cardiac ejection period, (dP/dT) can be calculated as the first derivative of the coronary venous pressure. In an example, the cardiac contractility sensor 204 can include a pressure sensor in one or more of the left ventricle, right ventricle, pulmonary artery, or aorta, and the rate of change of blood pressure can be calculated using information obtained from one or more of these pressure sensors. In an example, the cardiac contractility sensor 204 can include a heart sound sensor configured to detect an S1 heart sound, such as described or incorporated in Patangay et al., U.S. patent application Ser. No. 11/777,739 entitled "MONITORING OF HEART SOUNDS," now published as U.S. Patent Application Publication No. 2008/0119750, assigned to the assignee of the present patent application, the disclosure of which is incorporated herein by reference in its entirety. In an example, the cardiac contractility sensor 204 can include electrodes configured to sense intrinsic electrical heart activity, such as within a ventricle, such as alone or in combination with a PAP sensor or intracardiac impedance sensor. PEP, the time interval between sensed electrical activity within the ventricle (e.g. sensing of the "R" wave) and the onset of ventricular ejection of blood, can be measured from the sensed electrical event to the beginning of pressure increase in the pulmonary artery, using a PAP sensor, or can be measured to the beginning of an increase in intracardiac impedance, accompanying a decrease in ventricular volume during ejection, using electrodes positioned in the right or spanning the left ventricle. Measurement of PEP is further described or incorporated in Libbus, U.S. Pat. No. 7,509,166 entitled "AUTOMATIC BAROREFLEX MODULATION RESPONSIVE TO ADVERSE EVENT," assigned to the assignee of the present patent application, the disclosure of which is incorporated herein by reference in its entirety. In an example, the cardiac contractility sensor 204 can include electrodes for sensing an impedance, such as a transthoracic impedance, which can be used to determine cardiac stroke impedance, such as described or incorporated in Averina et al., U.S. Provisional Patent Application No. 61/228,745 entitled "BLOOD VOLUME REDISTRIBUTION THERAPY FOR HEART FAILURE," assigned to the assignee of the present patent application, the disclosure of which is incorporated herein by reference in its entirety. In an example, the cardiac contractility sensor 204 can include a cardiac force sensor configured to sense a force of cardiac contraction, such as described or incorporated in Zhang et al., U.S. patent application Ser. No. 11/559,702 entitled "CARDIAC FORCE SENSOR AND METHODS OF USE," now published as U.S. Patent Application Publication No. 2008/0114256, assigned to the assignee of the present patent application, the disclosure of which is incorporated herein by reference in its entirety.

In an example, the system 200 can further include a dyssynchrony sensor 206, which can be configured to detect an indication of intraventricular dyssynchrony from the subject such as by using an electrogram, an intracardiac impedance, an indication of heart wall motion, or a magnitude of a heart sound. Patients who exhibit both a CR and intraventricular dyssynchrony can demonstrate greater improvement in response to CRT therapy than patients who exhibit only dyssynchrony without a CR, or patients who exhibit neither dyssynchrony nor CR. Thus, an indication of dyssynchrony can be used in combination with CR to classify a patient as either therapy responders or non-responders.

The physical activity sensor 202, the cardiac contractility sensor 204, and the dyssynchrony sensor 206 can be coupled to the processor 208. The processor 208 can be configured to determine a CR indicator such as by using a characteristic of a function of the indication of cardiac contractility across various different physical activity levels of the subject. In an example, the processor can be configured to use physical activity signals detected by the physical activity sensor 202, such as to define time periods corresponding to different steady-state activity levels. The processor 208 can then determine a CR indicator such as by using a characteristic of a function of the indication of cardiac contractility across the different steady-state activity levels. Periods of steady-state activity can be identified by monitoring activity data (e.g. accelerometer or heart rate data) and deeming steady state to exist when the activity data meets one or more criteria. This can involve using systems or methods of ascertaining steady-state activity levels such as described or incorporated in Beck et al., U.S. patent application Ser. No. 11/184,327 entitled "METHODS AND APPARATUS FOR MONITORING PHYSIOLOGICAL RESPONSES TO STEADY STATE ACTIVITY," now published as U.S. Patent Application Publication No. 2007/0021678, assigned to the assignee of the present patent application, the disclosure of which is incorporated herein by reference in its entirety.

In an example, the processor 208 can be configured to determine a dyssynchrony indicator such as by using an indication of cardiac dyssynchrony detected by the dyssynchrony sensor 206. The processor 208 can further be configured to determine a diagnostic indicator such as by using both the dyssynchrony indicator and the CR indicator. Using the diagnostic indicator, the processor 208 can classify the subject as one of (1) a therapy responder or (2) a therapy non-responder. In an example, the processor 208 can classify the subject as one of (1) a therapy responder or (2) a therapy non-responder using only the CR indicator or only the dyssynchrony indicator.

The processor 208 can be coupled to a memory 210, which can be configured to receive and store the CR indicator, dyssynchrony indicator, or diagnostic indicator, and provide it to an automated process or to a user. For example, the memory can store the CR indicator and provide it to an external interface such as for use by a health care provider.

Additionally, the processor 208 can be coupled to a therapy circuit 212 configured to provide therapy to the subject. The therapy circuit 212 can include a cardiac resynchronization therapy (CRT) circuit, a neuromodulation therapy circuit, or a drug therapy control circuit, for example. The processor 208 can be configured to control therapy provided by the therapy circuit 212 such as by using information about the CR indicator. In an example, the processor 208 can be configured to trigger the therapy circuit 212 to provide therapy when the CR indicator indicates that the subject exhibits a CR that is above a specified threshold. In an example, the processor 208 can be configured to limit providing therapy to require that the CR indicator indicates that the subject exhibits a CR that exceeds the specified threshold, either alone, or in combination with another condition. Furthermore, in an example, the processor 208 can be configured to control the therapy circuit 212 to withhold therapy when the CR indicator indicates that the subject exhibits a CR that is below the same or a different specified threshold.

Figure 3A:
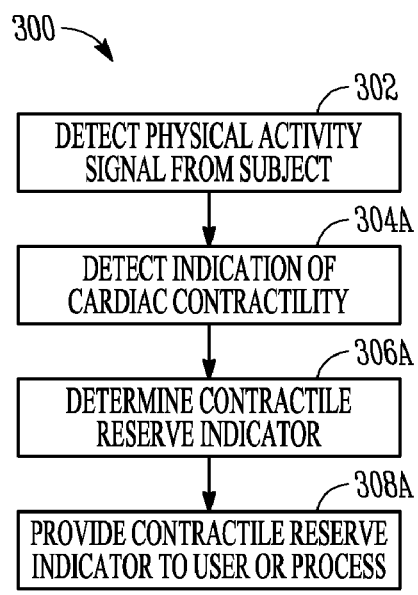
FIGS. 3A-3C are charts illustrating generally examples of methods for determining and using a contractile reserve indicator in diagnosis and therapy.
Figure 3B:
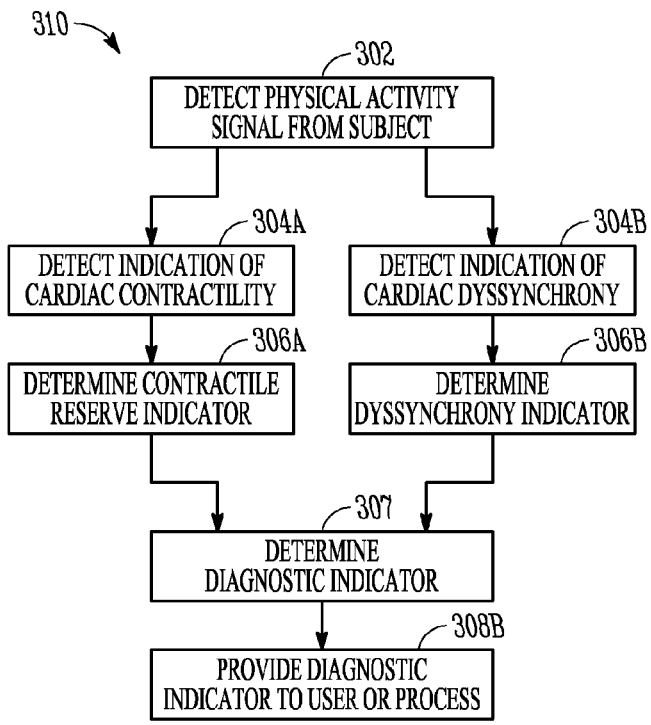
Figure 3C:
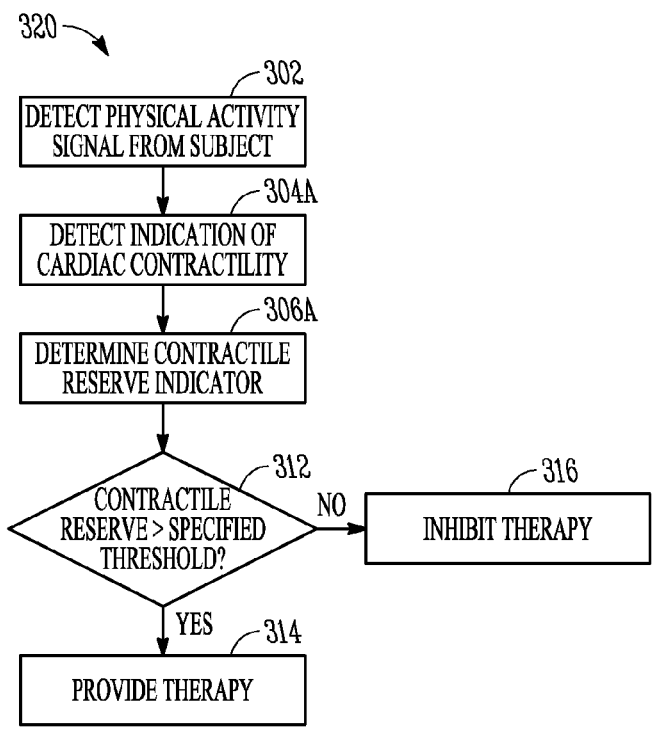

FIGS. 3A-3C are charts illustrating generally examples of methods for determining or using a CR indicator in diagnosis and therapy. FIG. 3A illustrates a method 300 for determining a CR indicator and providing the CR indicator to a user or process. At 302, a physical activity signal can be detected from the subject. An accelerometer or a heart rate sensor, for example, can be used as a physical activity sensor to detect the physical activity signal. A heart rate sensor can be used to detect the physical activity signal because changes in the subject's heart rate during activities of daily living can be reflective of changes in the subject's physical activity level. In an example, the physical activity signal can be used to define time periods corresponding to different steady-state activity levels, such as described above with respect to FIG. 2 above.

At 304A, an indication of cardiac contractility can be detected, such as by using at least one of a pulse pressure, a rate of change of blood pressure during a cardiac ejection period, a S1 heart sound magnitude, a PEP duration, or a change in cardiac stroke.

Pulse pressure, the difference between systolic and diastolic blood pressure, can be determined using PAP measurements, such as described in the above-incorporated U.S. patent application Ser. No. 11/624,974, now published as U.S. Patent Application Publication No. 2008/0177156. Pulse pressure can be used as an indicator of cardiac contractility. In general, as contractility increases, pulse pressure increases. It is believed that the increase in pulse pressure is due to an increase in stroke volume accompanying increased contractility.

A rate of change of blood pressure during a cardiac ejection period can be determined from pressures measured in a coronary vein, left ventricle, right ventricle, pulmonary artery, or aorta, for example. In general, as contractility increases, the rate of change of blood pressure increases. It is believed that the increase in the rate of change of blood pressure is due to an increase the strength of cardiac contraction, which, in turn, results from changes in cardiac muscle properties due to increased contractility.

S1 heart sound magnitude can be detected using a heart sound sensor, such as described in the above-incorporated U.S. patent application Ser. No. 11/777,739, now published as U.S. Patent Application Publication No. 2008/0119750. The S1 heart sound can be representative of the vibrational sound made as the atrioventricular valves close at the onset systole. S1 heart sound magnitude can be used as an indicator of cardiac contractility. In general, as contractility increases, the magnitude of the S1 heart sound increases. It is believed that the increase in magnitude of the S1 heart sound is due an increased volume of blood hitting the mitral and aortic valves at an increased velocity, which is caused by increased contractility.

PEP, the period of time between sensed electrical activity within the ventricle (e.g. sensing of the "Q" wave) and the onset of the S1 heart sound, can be detected using electrodes configured to sense electrical activity within a ventricle and a PAP sensor or intracardiac impedance sensor, as described in above incorporated U.S. Pat. No. 7,509,166. PEP can be used as an indicator or cardiac contractility. In general, as contractility increases, PEP decreases. It is believed that the decrease in PEP is due to decreased isovolumetric contraction time caused by increased contractility.

Cardiac stroke is representative of the change in blood volume in the heart during a cardiac cycle. Cardiac stroke can be determined, for example, using electrodes for sensing transthoracic impedance, from which cardiac stroke impedance can be derived, as described in above incorporated U.S. Provisional Patent Application No. 61/228,745. Other methods of determining cardiac stroke can include, for example, measuring a change in cardiac dimension with one or more miniature ultrasound sensors. In general, as contractility increases, cardiac stroke increases. It is believed that the increase in stroke is due to the ejection of an increased volume of blood at an increased velocity, which results from increased contractility. In an example, the velocity of ejection, which can be determined by dividing cardiac stroke by the ejection period, can also be used as an indication of contractility (e.g. increased velocity of ejection can indicate increased contractility).

At 306A, a CR indicator can be determined. The CR indicator can be determined using a characteristic of a function of the indication of cardiac contractility across different activity levels. For example, S1 heart sound magnitude can be used to determine the CR indicator. The magnitude of S1 heart sounds can be measured at multiple times during which the subject exhibits a variety of different physical activity levels. The S1 magnitude measurements can then be plotted against the corresponding activity levels (or heart rates) in order to determine a CR indicator, as further described below with respect to FIG. 6.

At 308A, the CR indicator can be provided to a user or process. The CR indicator can be provided to a health care provider, for example, via a local or remote interface. The health care provider can then use the CR indicator as an ambulatory assessment of patient status or as an assessment of patient response to therapy. The CR indicator can also be provided directly to a device for adjusting patient therapy parameters using the CR indicator. In an example, the CR indicator can be provided to a user or process serving as a screening tool for identifying a patient as either (1) a therapy responder or (2) a therapy non-responder using the CR indicator.

FIG. 3B illustrates a method 310 for determining a diagnostic indicator and providing the diagnostic indicator to a user or process. At 302, a physical activity signal can be detected from the subject, as described above with respect to FIG. 3A. At 304A an indication of cardiac contractility can be detected, and at 306A a CR indicator can be determined, as described above with respect to FIG. 3A. At 304B, an indication of cardiac dyssynchrony can be detected. In an example, an indication of cardiac dyssynchrony can be detected using at least one of an electrocardiogram, an intracardiac impedance measurement, an indication of heart wall motion, or a magnitude of a heart sound. At 306B, a dyssynchrony indicator can be determined using the indication of cardiac dyssynchrony. At 307, a diagnostic indicator can be determined using both the CR indicator and the dyssynchrony indicator. Patients who exhibit both a CR and intraventricular dyssynchrony can demonstrate greater improvement in response to CRT therapy than patients who exhibit only dyssynchrony without a CR, or patients who exhibit neither dyssynchrony nor CR. Thus, the diagnostic indicator can be used to classify a patient as either (1) a therapy responder or (2) a therapy non-responder. At 308B, the diagnostic indicator can be provided to a user or process, in a manner similar to that described above with respect to 308A in FIG. 3A.

FIG. 3C illustrates a method 320 for controlling therapy using information about the CR indicator. As described above with respect to FIG. 3A, a physical activity signal can be detected from a subject at 302, an indication of cardiac contractility can be detected at 304A, and a CR indicator can be determined at 306A. In an example, a dyssynchrony indicator and a diagnostic indicator can be determined as described above with respect to FIG. 3B. At 312, the CR indicator can be compared to a specified threshold value. In an example, a dyssynchrony indicator or a diagnostic indicator can be used in addition to or in place of the CR indicator in step 312. At 314, if the CR indicator is above the specified threshold value, therapy can be provided to the subject. A subject with a CR indicator above the specified threshold can be considered to be a therapy responder. Such a subject can be more likely to benefit from therapy than a subject whose CR indicator is below the specified threshold value. The therapy provided can include at least one of CRT, neuromodulation therapy, or drug therapy, for example. These therapies can be aimed at preventing cardiac remodeling and improving cardiac performance. At 316, if the CR indicator is below the specified threshold value, therapy can be withheld from the subject. A subject with a CR indicator below the specified threshold can be considered to be a therapy non-responder. Such a subject can be less likely to benefit from therapy, such as CRT, than a subject whose CR indicator is above the specified threshold value. Thus, alternative treatment methods, other than CRT, neuromodulation, or drug therapy, may be sought for subjects deemed to be therapy non-responders.

Figures 4, 5:
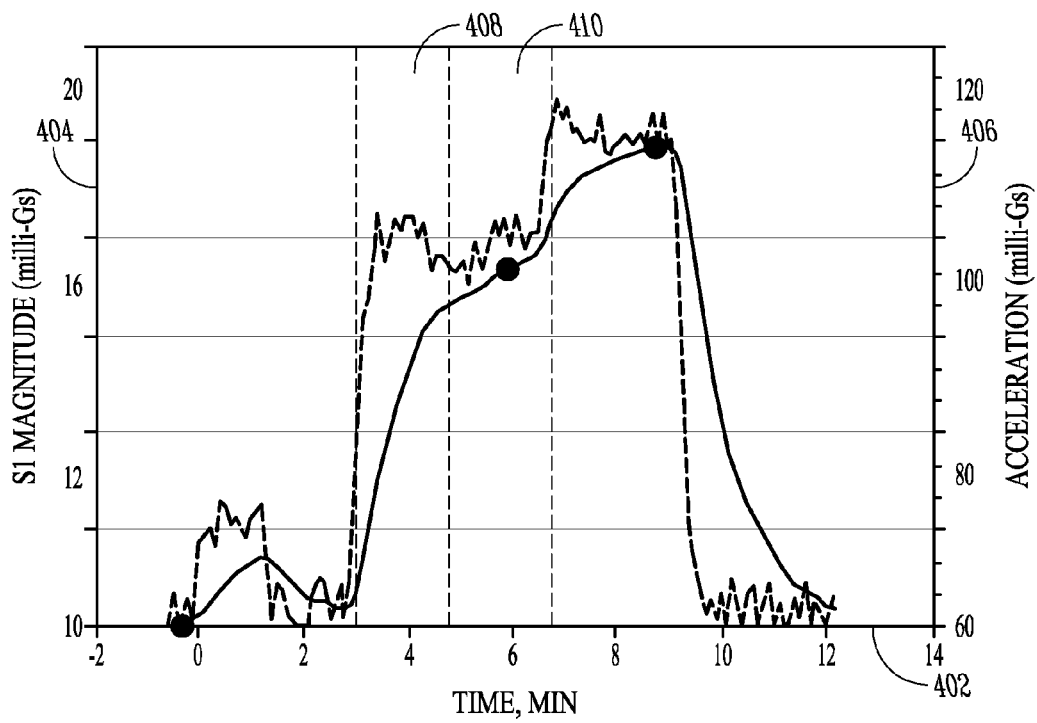
FIG. 4 is a graph illustrating generally an example of a cardiac contractility indication (e.g. S1 magnitude) and physical activity level (e.g. heart rate) plotted against time.
FIG. 5 is a table illustrating generally an example of data representative of indications of cardiac contractility during steady-state activity levels.

FIG. 4 is a graph illustrating generally an example of a cardiac contractility indication (e.g. S1 magnitude) and physical activity level (e.g. heart rate) plotted against time. The x-axis, 402, represents time measured in minutes. The first y-axis, 404, represents S1 magnitude measured in milli-G's (thousandths of gravitational acceleration ($9.8$ m/s$^2$). The second y-axis, 406, represents activity level measured as acceleration (in milli-G's). In an example, activity level can be measured as heart rate (in beats per minute (bpm)) or minute ventilation (in liters/minute) instead of, or in addition to, heart rate. The plot shows a lag between detected steady-state activity and steady-state S1 magnitude. In an example, for the purpose of using physiological data such as S1 magnitude to provide an indication of cardiac contractility, physical activity is deemed to be at a steady state after the detected physical activity has been in a specified range for a specified period of time. In an example, the specified period of time is about two or three minutes. For example, FIG. 4 shows a time period 410 from around minute 5 to minute 7, which is considered a steady-state physical activity level. The graph shows steady-state activity between about 100 bpm and 110 bpm during the time period 410. The time period 408 from around minute 3 to minute 5 also shows constant detected activity in this range. In an example, the two minute period 408 from minute 3 to minute 5 qualifies the following period 410 for consideration as steady-state activity. This allows time for the S1 magnitude to reach a steady state after the detected activity level has reached a steady state. For example, the plot of S1 magnitude against time shows that the S1 magnitude moves to a steady state value of around 16 milli-G's at point 412 during the period 410 from minute about 5 to minute 7. In contrast, during time period 408, the S1 magnitude is not steady state, but moves from about 10 milli-G's to around 16 milli-G's.

FIG. 5 is a table illustrating generally an example of data representative of indications of cardiac contractility during steady-state activity levels. These data can be obtained, for example, using activity and physiological data such as that derived from the graph illustrated in FIG. 4. Furthermore, these data can be obtained according to the methods disclosed in previously incorporated U.S. patent application Ser. No. 11/184,327, now published as U.S. Patent Application Publication No. 2007/0021678, including methods of monitoring physiological responses to steady-state activity. For example, data can be collected during activities of daily living (e.g. walking, climbing stairs, sitting, sleeping, etc.), in which a patient will exhibit a variety of steady-state activity levels.

The first two columns in the table list steady-state activity levels. The first column is activity measured as acceleration in milli-Gs. The second column is heart rate measured in beats per minute (bpm). Columns 3-5 list physiological data representative of cardiac contractility. The third column is S1 magnitude measured in milli-G's. The fourth column is pulse pressure measured in millimeters of mercury (mmHg). The fifth column is the rate of change of blood pressure during a cardiac ejection period (dP/dT) measured in mmHg/second.

Figure 6:
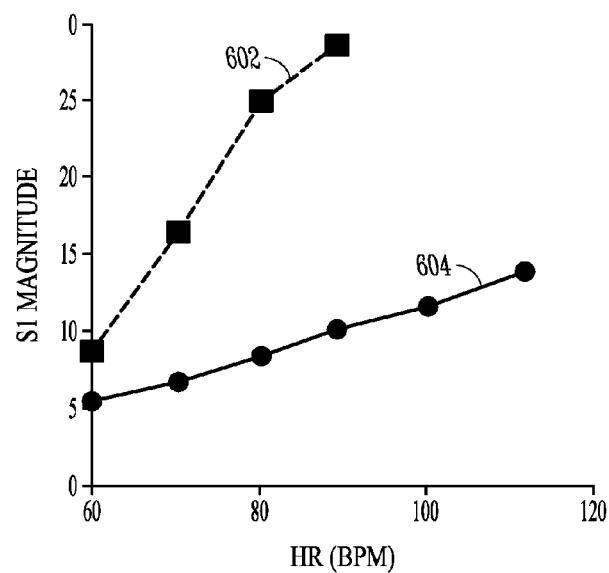
FIG. 6 is two graphs illustrating generally an example of contractility indication data plotted against heart rate.

Data from the table in FIG. 5 can be used to determine a CR indicator. For example, as shown in FIG. 6, an indication of CR can be determined by plotting the values of S1 magnitude (or any other indication of cardiac contractility) against the corresponding steady-state activity levels (e.g. heart rate), and calculating the approximate slope of the line. The slope can be an indication of CR, or the maximum change in contractility that can be achieved by a subject.

In FIG. 6, the line 602 can represent data from a patient with a relatively high CR. In contrast, the line 604 can represent data from a patient with a relatively low CR. As the steady-state activity level (measured in this example as HR) increases, contractility (measured in this example as S1 magnitude) increases more rapidly in the patient with a higher CR (line 602) than in the patient with a lower CR (line 604). This can be seen from the steeper slope of line 602 compared to line 604. In an example, the slope of data points in a plot of contractility against activity, such as that in FIG. 6, can be calculated using linear or non-linear regressions. Examples of non-linear regressions include parabolic, logarithmic, or exponential regressions.

Figure 7:
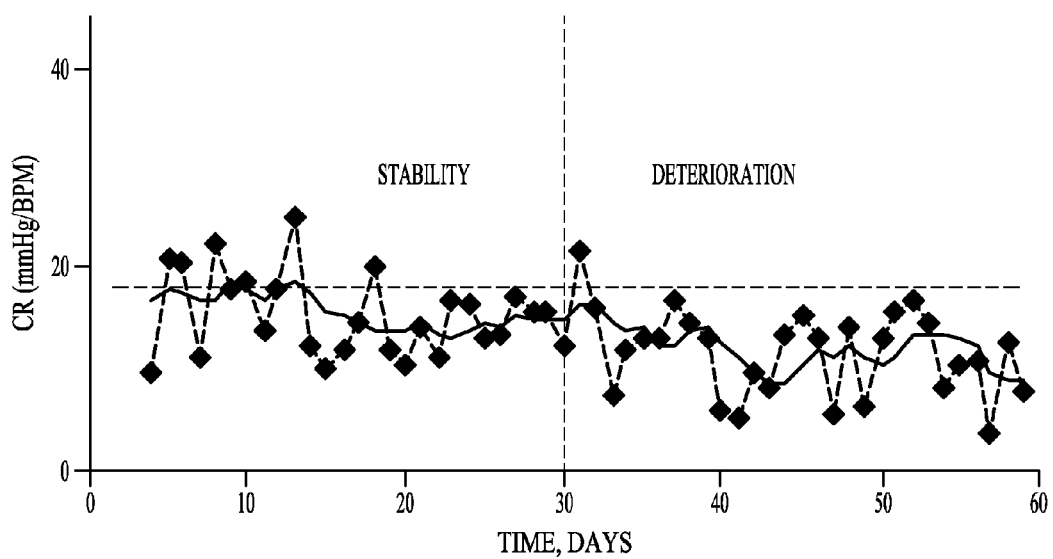
FIG. 7 is a graph illustrating generally an example of contractile reserve plotted against time.

CR values, such as those obtained from the slopes of the lines in FIG. 6, can be used to create a graph of CR plotted against time, an example of which is generally illustrated in FIG. 7. Such a graph can be used to assess patient status and to adjust CRT or other therapy accordingly, as previously disclosed. In FIG. 7, time (in days) is plotted on the x-axis and CR is plotted on the y-axis. In this example, CR has been determined using S1 magnitude as a measure of contractility and heart rate as a measure of activity. Thus, CR is measured in milli-G's/BPM. As can be seen from the graph in FIG. 7, CR is about 20 milli-G's/BPM from about day 3 to about day 13, and about 15 milli-G's/BPM from about day 13 to about day 30. The period of time from day 3 to 30 is labeled "stability" because the patient exhibits a relatively high CR during this period, which can be indicative of a greater ability of the heart to reverse remodeling and improve performance. However, after day 30, CR begins to decrease and become more sporadic, ranging from about 10-15 milli-G's/BPM. This time period, from day 30 to day 60, is labeled "deterioration" because the lower CR can be predictive of a lesser ability of the patient's heart to reverse remodeling and improve performance in response to CRT or other therapies.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. A system comprising:
   a physical activity sensor, configured to detect a physical activity signal from a subject;
   a cardiac contractility sensor, configured to detect an indication of cardiac contractility from the subject;
   a processor, coupled to the cardiac contractility sensor and the physical activity sensor, the processor configured to determine a contractile reserve indicator using a characteristic of a function of the indication of cardiac contractility across various different activity levels, wherein the contractile reserve indicator corresponds to a predicted value of a maximum change in contractility that can be achieved by the subject; and
   a memory, coupled to the processor and configured to receive and store the contractile reserve indicator to be provided to a process or a user.

2. The system of claim 1, wherein the processor is configured to use the physical activity signal to define time periods corresponding to different steady-state activity levels, and wherein the processor is configured to determine the contractile reserve indicator using a characteristic of a function of the indication of cardiac contractility across the different steady-state activity levels.

3. The system of claim 1, wherein the cardiac contractility sensor is configured to detect the indication of cardiac contractility using at least one of: a pulse pressure, a rate of change of blood pressure during a cardiac ejection period, a rate of change of intraventricular blood pressure during a cardiac ejection period, a S1 heart sound magnitude, a pre-ejection period, or a change in cardiac stroke.

4. The system of claim 1, wherein the processor is configured to classify the subject as one of (1) a therapy responder or (2) a therapy non-responder using the contractile reserve indicator.

5. The system of claim 1, comprising:
   a dyssynchrony sensor configured to detect an indication of cardiac dyssynchrony from the subject, the dyssynchrony sensor coupled to the processor;
   wherein the processor is configured to:
      determine a dyssynchrony indicator using the indication of cardiac dyssynchrony; and
      determine a diagnostic indicator using both the dyssynchrony indicator and the contractile reserve indicator; and
   wherein the memory is coupled to receive and store the diagnostic indicator to be provided to a user or process.

6. The system of claim 5, wherein the dyssynchrony sensor is configured to detect an indication of cardiac dyssynchrony using at least one of an electrocardiogram, an intracardiac impedance, an indication of heart wall motion, or a magnitude of a heart sound.

7. The system of claim 1, comprising a therapy circuit, coupled to the processor, the therapy circuit configured to provide a therapy to the subject;
and wherein the processor is configured to control the therapy provided by the therapy circuit using information about the contractile reserve indicator.

8. The system of claim 7, wherein the therapy circuit includes at least one of a cardiac resynchronization therapy circuit, a neuromodulation therapy circuit, or a drug therapy control circuit.

9. The system of claim 7, wherein the processor is configured to trigger the therapy circuit to provide therapy when the contractile reserve indicator indicates that the subject exhibits a contractile reserve that is above a specified threshold.

10. The system of claim 7, wherein the processor is configured to trigger the therapy circuit to withhold therapy when the contractile reserve indicator indicates that the subject exhibits a contractile reserve that is below a specified threshold.

11. A method comprising:
    detecting a physical activity signal from a subject; and
    detecting an indication of cardiac contractility from the subject;
    determining a contractile reserve indicator using a characteristic of a function of the indication of cardiac contractility across various different activity levels, wherein the contractile reserve indicator corresponds to a predicted value of a maximum change in contractility that can be achieved by the subject; and
    providing the contractile reserve indicator to a user or process.

12. The method of claim 11 comprising:
    using the physical activity signal to define time periods corresponding to different steady-state activity levels; and
    wherein determining a contractile reserve indicator includes using a characteristic of a function of the indication of cardiac contractility across the different steady-state activity levels.

13. The method of claim 11, wherein detecting an indication of cardiac contractility includes using at least one of: a pulse pressure, a rate of change of blood pressure during a cardiac ejection period, a rate of change of intraventricular blood pressure during a cardiac ejection period, a S1 heart sound magnitude, a pre-ejection period, or a change in cardiac stroke.

14. The method of claim 11 comprising classifying the subject as one of (1) a therapy responder or (2) a therapy non-responder using the contractile reserve indicator.

15. The method of claim 11, comprising:
    detecting an indication of cardiac dyssynchrony from the subject;
    determining a dyssynchrony indicator using the indication of cardiac dyssynchrony;
    determining a diagnostic indicator using both the dyssynchrony indicator and the contractile reserve indicator; and
    providing the diagnostic indicator to a user or process.

16. The method of claim 15, wherein detecting an indication of dyssynchrony includes using at least one of an electrocardiogram, an intracardiac impedance, an indication of heart wall motion, or a magnitude of a heart sound.

17. The method of claim 11, comprising:
    providing a therapy to the subject; and
    controlling the therapy using information about the contractile reserve indicator.

18. The method of claim 17, wherein providing the therapy includes providing at least one of cardiac resynchronization therapy, neuromodulation therapy, or drug therapy.

19. The method of claim 17, comprising providing the therapy to the subject when the contractile reserve indicator indicates that the subject exhibits a contractile reserve that is above a specified threshold.

20. The method of claim 17, comprising withholding the therapy from the subject when the contractile reserve indicator indicates that the subject exhibits a contractile reserve that is below a specified threshold.

* * * * *